United States Patent [19]

Mantz et al.

[11] Patent Number: 4,937,448

[45] Date of Patent: Jun. 26, 1990

[54] SELF-NORMALIZING SINGLE-BEAM LASER SPECTROMETER

[75] Inventors: Arlan W. Mantz, Acton; John C. O'Connell, Andover, both of Mass.

[73] Assignee: Spectra-Physics, Inc., San Jose, Calif.

[21] Appl. No.: 199,241

[22] Filed: May 26, 1988

[51] Int. Cl.$^5$ .......................... G01J 1/00; G01J 3/42
[52] U.S. Cl. .................................. 250/343; 250/344; 250/345; 356/324; 356/325
[58] Field of Search ...................... 250/343, 344, 345; 356/323, 324, 325

[56] References Cited

U.S. PATENT DOCUMENTS

| | | | |
|---|---|---|---|
| 3,679,899 | 7/1972 | Dimeff | 250/343 |
| 3,732,017 | 5/1973 | Wolber | 250/343 |
| 3,899,252 | 8/1975 | Dimeff | 250/343 |
| 4,068,953 | 1/1978 | Harney et al. | 356/75 |
| 4,156,571 | 5/1979 | Ljung | 356/445 |
| 4,196,402 | 4/1980 | Butler et al. | 331/94.5 |
| 4,242,584 | 12/1980 | Krieg et al. | 250/423 |
| 4,272,734 | 6/1981 | Jarrett et al. | 331/94.5 |
| 4,381,923 | 5/1983 | Wada | 23/293 |
| 4,410,273 | 10/1983 | Mantz et al. | 356/319 |
| 4,462,686 | 7/1984 | Bridges | 356/318 |
| 4,634,864 | 1/1987 | Lucatorto et al. | 250/282 |

OTHER PUBLICATIONS

John A. Mucha, *Standard Addition Technique for Quantitative Trace Gas Analysis Using Derivative Infrared Diode Laser Spectroscopy*, 30 Nov. 81, vol. 36, No. 4, 1982 of Applied Spectroscopy, pp. 393–400.

*SP 5100 Isotope Ratio Measurement System*, wall eng and Mantz Spectra Physics, Laser Analysis Div., 25 Wiggins Ave., Bedford MA 01730.

Dual Beam, Second Derivative Tunable Diode Laser Infrared Spectroscopy Applied to Trace Gas Measurement; David R. Tallant, Rudolph G. Jungst Sandia National Laboratories.

Standard Addition Technique for Quantitative Trace Gas Analysis Using Derivative Infrared Diode Laser Spectroscopy; John A. Mucha, Applied Spectroscopy, vol. 36, No. 4, 1982.

Calibration of diode-laser second-derivative modulation spectrometry with a reference cell; Claus Weitkamp, Applied Optics, vol. 23, No. 1, 1 Jan., 1984.

High Sensitivity Pollution Detection Employing Tunable Diode Lasers; J. Reid, J. Shewchun, B. K. Garside, and E. A. Ballik; Applied Optics, vol. 17, No. 2, 15 Jan. 1978.

Tunable Diode Laser Spectroscopy: an invited review; R. S. Eng., J. F. Butler, K. J. Linden, Optical Engineering vol. 16, No. 6 Nov./Dec. 1980.

SP5100 Isotope Ratio Measurement System; D. L. Wall, R. S. Eng. & A. W. Mantz; Spectra-Physics, Laser Analytics Division.

Second Derivative Tunable Diode Laser Spectrometry for Line Profile Determination, II. Experimental Results; David L. Grieble, Mark L. Olson, Jeffrey N-P. Sun & Peter R. Griffiths, Applied Spectroscopy, vol. 34, No. 1, 1980.

*Primary Examiner*—Constantine Hannaher
*Assistant Examiner*—J. Eisenberg
*Attorney, Agent, or Firm*—Allegretti & Witcoff, Ltd.

[57] ABSTRACT

Self-normalization of laser spectrometers is provided by I"/I laser modulation and detection. A single tunable diode laser is frequency modulated by a high S/N ratio triangle wave, mechanically chopped, passed through an isothermal in-line gas and reference chamber absorption cell, and synchronously detected to provide the I" and I signals. The preferred embodiment discloses isotopic ratio measurements. The invention has application to quantitative trace gas measurements generally.

4 Claims, 2 Drawing Sheets

SELF-NORMALIZING SINGLE-BEAM LASER SPECTROMETER

FIELD OF THE INVENTION

This invention is directed to the field of infrared absorption spectroscopy, and more particularly, to a novel self-normalizing single-beam laser spectrometer.

BACKGROUND OF THE INVENTION

Laser spectroscopy takes advantage of the laser lines produced by lead salt, III-V compound materials, and other substances to probe the wavelength region between one and 30 micrometers, the so-called infrared fingerprint region, in which the characteristic vibration-rotation lines for most molecules are located. The laser is tuned to the appropriate frequency corresponding to the absorption feature of a species of interest, and passed through a sample gas to be probed. The sample gas absorbs the emitted radiation in characteristic ways dependent on the presence therein of the species of interest. It is thus possible to analyze trace gases with a very high resolution such as for air pollution monitoring, chemical laser systems diagnosis, among others.

In practical laser spectrometry systems heretofore, the laser absorption is sensitively dependent on the prevailing temperature, optical, and electronic conditions of the spectrometry instrument. In the heretofore known dual-beam laser spectrometers, as that disclosed, for example, in commonly assigned U.S. Pat. No. 4,410,273 incorporated herein by reference, the beam dividing optics, the separate sample and reference cells, the different sample and reference beams, and the different detectors provided for the reference absorption and sample absorption measurements each introduce and combine to introduce variables that must be painstakingly compensated. Otherwise, changes in intensity of the measured signal may not reflect absorption by the species of interest but rather differential drift of the different sample and reference detectors, variable absorbency due to the differences in temperature between the reference and sample cells, and differences in the sample and reference beams introduced by the optics. The compensation procedures that must be employed to neutralize such effects not only are bothersome and time consuming, but notwithstanding such procedures, there still is present some element of uncertainty in the resolution with which the measurements are taken.

In addition to the compensation of the effects of the instrument, the measured data must be normalized to the intensity of the tunable laser source so that from that reference the true concentration of gas may be calculated. In the heretofore known laser spectrometers, normalization was typically required either prior to or after laser absorption measurements. But, among other disadvantages, the normalization procedure would often require separate standard sample measurements and the consumption of specially prepared and expensive standard normalization samples.

SUMMARY OF THE INVENTION

The present invention contemplates as one of its objects a laser spectrometer that is substantially desensitized to the extreme temperature and component dependence of absorption spectra that was characteristic of the heretofore known devices, and discloses in accordance therewith a laser spectrometer having a tunable laser source, a combination in-line reference and sample absorption cell, and a single detector. The combination reference and sample cell includes a reference chamber and a tandem sample chamber in longitudinally abutting relation. The in-line absorption cell is in thermodynamic equilibrium so that isothermal temperature conditions prevail in the reference chamber and sample chamber thereof. The same detector detects the tunable single laser beam after having passed through the in-line absorption cell. The present invention thereby totally eliminates the errors of the measured absorption spectra which may result from small variations.

The present invention further contemplates as another of its objects a self-normalizing laser spectrometer not requiring that the intensity of the laser emission of the tunable laser be determined in a separate normalization step and discloses in accordance therewith $I''/I$ laser modulation and synchronous detection by which both laser power fluctuations and detector drifts self-cancel to yield self-normalized absorption spectra directly and without the heretofore necessary and separate normalization step. The tunable laser lines are frequency modulated, and the frequency modulated laser lines are mechanically chopped at a preselected chopper frequency. The detector output signal is synchronously detected at the chopper frequency to provide the $I$ signal, and the detector signal is synchronously detected at first and second harmonics of the frequency modulated tunable laser lines to provide an $I'$ signal and the $I''$ signal. The ratio of the $I''$ signal with the $I$ signal is representative of concentration of the species of interest. The $I'$ signal is fed back to stabilize the tunable laser emission at the center frequency of the absorption line of the species of interest.

In the preferred embodiment, the self-normalizing single-beam laser spectrometer of the present invention is disclosed in the context of providing isotope ratios, such as $C_{12}/C_{13}$ determinations. The present invention has utility in other applications for laser spectroscopy including but not limited to trace gas analysis, as for process monitoring systems and other gas measurement or monitoring systems.

BRIEF DESCRIPTION OF THE DRAWINGS

These and other objects, advantages and aspects of the present invention will become apparent as the invention becomes better understood by referring to the following detailed description thereof, and to the drawings, wherein.

DETAILED DESCRIPTION OF THE INVENTION

Figure 1:
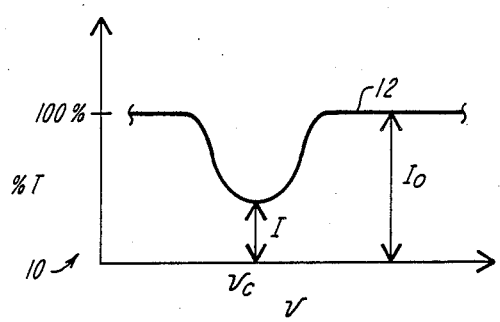
FIG. 1 is a graph useful in explaining the principle of the $I''/I$ laser modulation and detection technique of the present invention.

Referring now to FIG. 1, generally designated at 10 is a diagram useful in explaining the principle of the $I''/I$ laser modulation and detection technique according to the present invention. A graph 12 is plotted with percent transmission designated "%T" as the value of the ordinate and with frequency designated "$\nu$" as the abscissa value. For a given laser line, the tunable laser output has an intensity designated "$I_0$". The selected laser line is absorbed by the corresponding absorption characteristic of the molecular species of interest, and its intensity designated "I" exhibits a minimum at a frequency center designated "$\nu_C$". Unlike the heretofore known laser spectrometers, in which the intensity "$I_0$" had had to be determined in a separate, and somewhat unreliable procedure in order to provide data normalization, the laser modulation and detection technique of the instant invention as appears more fully hereinbelow provides self-normalization, and thus significantly improves over the heretofore required normalization procedures.

The absorption intensity as a function of frequency can be written:

$$I(\nu) = I_0 e^{-\alpha(\nu)clp} \quad (1)$$

where "c" is the concentration to be measured, "1" is a fixed pathlength predetermined for a given absorption cell, "p" is the pressure in the absorption cell, and "$\alpha(\nu)$" is $1(\nu-\nu_0)^2 + \alpha^2$ for Lorenzian lines. Taking the first derivative of equation 1, we have:

$$\frac{dI}{d\nu} = -clp\, I_0 e^{-\alpha(\nu)clp} \quad (2)$$

The first derivative of $\alpha$ with respect to $\nu$ is:

$$\frac{d\alpha}{d\nu} = \frac{-2(\nu - \nu_o)}{[(\nu - \nu_o)^2 + \alpha^2]^2} \quad (3)$$

and at the line center, $\nu_c$, the first derivative of $\alpha(\nu)$ is zero, so that the first derivative of I with respect to $\nu$ at the line center is also equal to zero.

The second derivative of Equation 1 is:

$$\frac{d^2I}{d\nu^2} = (clp)^2 I_0 e^{-\alpha(\nu)clp}\left(\frac{d\alpha}{d\nu}\right)^2 - clp I_0 e^{-\alpha(\nu)clp}\left(\frac{d^2\alpha}{d\nu^2}\right) \quad (4)$$

where, the second derivative of $\alpha(\nu)$ is:

$$\frac{d^2\alpha}{d\nu^2} = \frac{-2}{[(\nu - \nu_o)^2 + \alpha^2]^2} + \frac{8(\nu - \nu_o)^2}{[(\nu - \nu_o)^2 + \alpha^2]^3} \quad (5)$$

at the line center, the second derivative of the intensity with respect to $\nu$ is:

$$\frac{d^2I}{d\nu^2} = -clp\, I_0 e^{-\alpha(\nu)clp}\left[\frac{-2}{\alpha^4}\right] \quad (6)$$

and substituting I for the right hand term of Equation 1, the second derivative of the intensity is:

$$\frac{d^2I}{d\nu^2} = clp\, I\left[\frac{-2}{\alpha^4}\right] \quad (7)$$

upon term rearrangement, $$\frac{\frac{d^2I}{d\nu^2}}{I} = clp\left(\frac{-2}{\alpha^4}\right) = \frac{I''}{I} \quad (8)$$

from which it is evident that the $I''/I$ ratio is directly Proportional to the desired concentration of the molecular species of interest.

Figure 2:
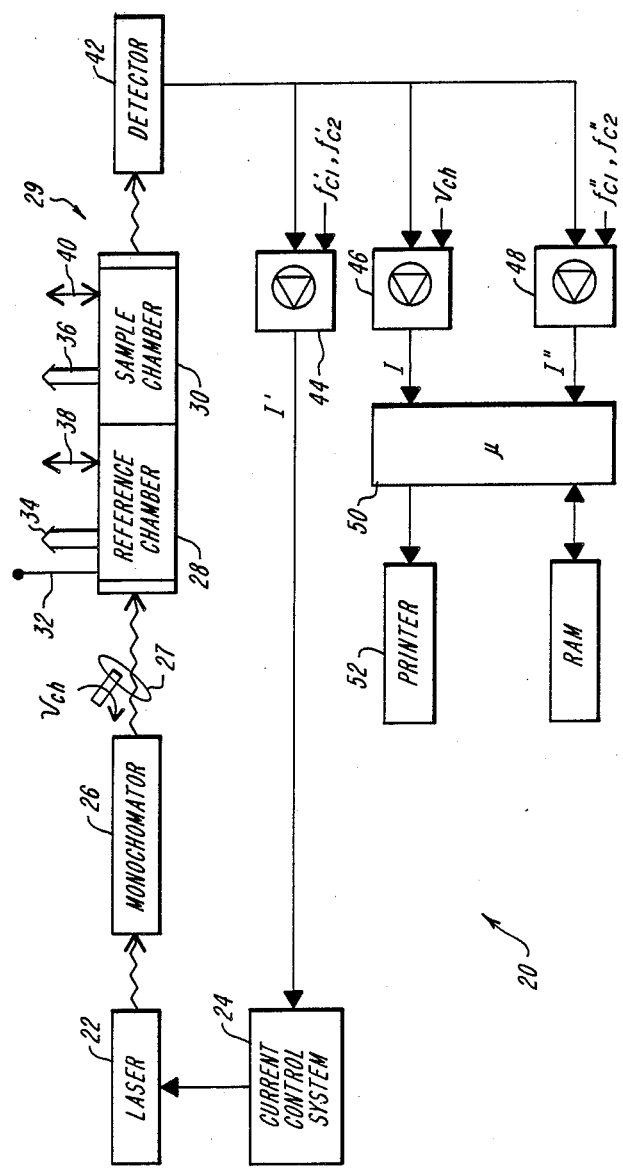
FIG. 2 is a block diagram illustrating the self-normalizing single-beam laser spectrometer constructed in accordance with the present invention.

Referring now to FIG. 2, generally designated at 20 is a block diagram of an exemplary isotopic laser spectrometer embodying the $I''/I$ laser modulation and synchronous detection principle of the present invention. As will be appreciated, the isotopic measurement spectrometer is exemplary only, the present invention having application to trace gas analysis spectroscopy generally, and is not limited to isotopic measurement systems.

A temperature controlled laser 22 is operative to provide laser emission tunable throughout the wavelength region substantially between three and thirty micrometers to probe the absorption spectra of molecular species of interest, such as $C_{12}/C_{13}$ isotopic ratios. The tunable laser 22 in the preferred embodiment is a lead salt tunable diode laser, the laser pump of which is a P-N junction semiconductor formed in a selected composition of a lead salt crystal, which is typically shaped as a rectangular parallelopiped. Ohmic contacts are attached to the polished surfaces of the crystal, and the diode is mounted to a copper stud. The diode is cooled to cryogenic temperatures, by any suitable means, and a forward bias applied to the diode produces spontaneous emission at a wavelength determined by the energy gap of the semiconductor. Preferably, the SP5600 tunable diode laser manufactured and marketed by the instant assignee is employed.

The emission frequency of the tunable diode laser 22 is preferably current and temperature controlled, as by a voltage controlled current source 24, preferably the SP 5820 laser current control module manufactured and marketed by the instant assignee. As will be appreciated by those skilled in the art, the P-N junction of the laser diode is heated as the current therethrough is increased, which affects the energy gap and crystal refractive index, and therewith the output frequency. In the preferred embodiment, the current controller 24 is part of a feedback loop which is responsive to a signal I', to be described, to lock the tunable laser to the center frequency of each laser line of interest in a manner well known to those skilled in the art, and as disclosed, for example, in commonly assigned U.S. Pat. No. 4,410,273, incorporated herein by reference. Other laser frequency tuning mechanisms are possible as well, such as by varying the temperature of the diode, by applying an external magnetic field, and/or by varying the hydrostatic pressure.

Figure 3:
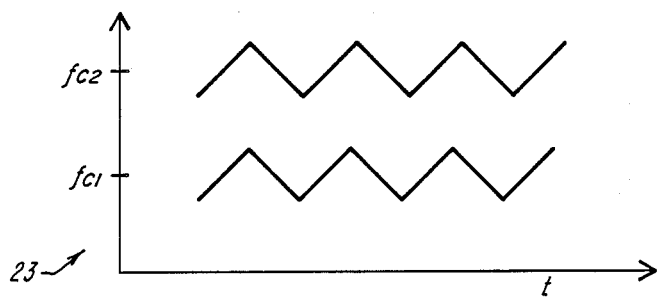
FIG. 3 is a graph useful in illustrating the laser modulation used in the laser spectrometer of FIG. 2.

For isotopic ratio concentration measurements, and referring now briefly to FIG. 3, generally designated at 23 is a graph useful in illustrating the laser modulation of the laser spectrometer of the FIG. 2 embodiment. The tunable laser 22 (FIG. 1) is selectively modulated alternatively first about the center frequency $f_{c1}$, then about the center frequency $f_{c2}$, of the isotopic species of interest, as for the $C_{12}/C_{13}$ isotopes. The modulation has an amplitude swing large enough to sweep the half power width of the corresponding isotopic absorption bands, and has a frequency determined by the characteristics of the detector. In the usual case, the frequency is selected to be between 500 Hz and ten kilohertz, 6.6 kilohertz being presently preferred. A triangle shape, as illustrated, has been found to provide an excellent signal to noise ratio, although other waveform shapes can be employed as well without departing from the inventive concept.

Returning now to FIG. 2, a monochrometer 26 is provided to filter the emission of the tunable laser 16. While any monochrometer that provides a selected narrowband output wavelength radiation may be employed, it is preferred that the monochrometer model SP515 manufactured and marketed by the instant assignee be employed.

A mechanical chopper 27 is provided in the optical path of the tunable laser emission. The chopper 27 preferably has a fifty percent duty cycle, and a 400Hz frequency of cycling. Other suitable frequencies may be employed as well without departing from the inventive concept.

An in-line absorption cell generally designated 29 is provided to receive the mechanically chopped frequency modulated emission of the frequency tunable diode laser 22. The cell 29 includes a reference chamber 28 in longitudinally abutting relation with a sample chamber 30, so that the tunable laser beam passes first through the reference gas in the chamber 28 and then through the sample gas in the chamber 30 where it is multiply reflected and returned back through the reference cell 28. A single pass absorption cell may also be utilized in combination with a single pass reference cell. A temperature controller schematically illustrated at 32 keeps the in-line reference chamber 28 and sample chamber 30 in thermodynamic equilibrium, so that the same temperature conditions prevail in both chambers 28, 30, thereby substantially eliminating any temperature induced measurement variabilities. The sample cell may be a so-called White cell to provide the multiple reflections, or an ordinary single pass cell in the alternative embodiment. The reference chamber 28 and sample chamber 30 are connected in the usual way to vacuum, as schematically illustrated by arrows 34, 36, and gas injection and removal ports are provided in the usual way as schematically illustrated by the arrows 38 and 40.

A temperature controlled detector 42 is positioned along the optical path of the tunable laser beam and at the reflected output of the tandem absorption cell 29. Any suitable detector 42, responsive to the infrared frequency region of interest, may be employed In the preferred embodiment, the detector 42 may advantageously be a thermoelectrically cooled PbSe detector or cryogenically cooled InSb detector model No. SP 5911 manufactured and marketed by the instant assignee.

A first synchronous detector 44 is electrically connected to the output of the temperature controlled detector 42. The synchronous demodulator 44 mixes the detector signal with a first harmonic ($f'_{c1}$, $f'_{c2}$) of the laser modulation frequency to provide the I' signal. In the isotope ratio concentration determination of the illustrated embodiment, the synchronous detector 44 detects the output signal at the frequencies designated $f'_{c1}$, $f'_{c2}$. The current source 24 is operative in response to the I' signal as already described to lock the frequency of each of the tunable laser 22 to the center frequency of the absorption lines of interest, thereby compensating for any drifting in frequency that may occur.

A second synchronous demodulator 46 is connected to the output of the detector 42. The detector 46 mixes the detector signal with the chopping frequency $\nu_{ch}$ to provide the signal I.

A third synchronous demodulator 48 is connected to the output of the detector 42. The synchronous detector 48 mixes the detector signal with a signal at the second harmonic of the laser modulation frequency to provide the signal I''.

In the illustrated $C_{12}/C_{13}$ isotope ratio determination the synchronous detector 48 detects the output signal at the frequencies designated $f''_{c1}$, $f''_{c2}$.

As will readily be appreciated by those skilled in the art, the signals I'' and I'' mathematically reflect the first and second order derivatives of the laser absorption intensity signal output of the detector.

A processor 50 is operatively connected to receive the I'' and I signals. The processor 50 includes RAM and ROM associated therewith in the usual manner. The processor responds to the I'' and I signaling and is operative to compute their ratio, through which as described above the desired concentration is readily obtained. The signal $I''/I$ is self-normalized, any variation attributable to laser power fluctuations and/or to detector level drifts being already cancelled by virtue of the synchronous demodulation at the optical chopper frequency and at the second harmonics of the laser modulation frequencies.

A printer or other data storage device 52 is provided for recording the calculated concentration ratios.

Figure 4:
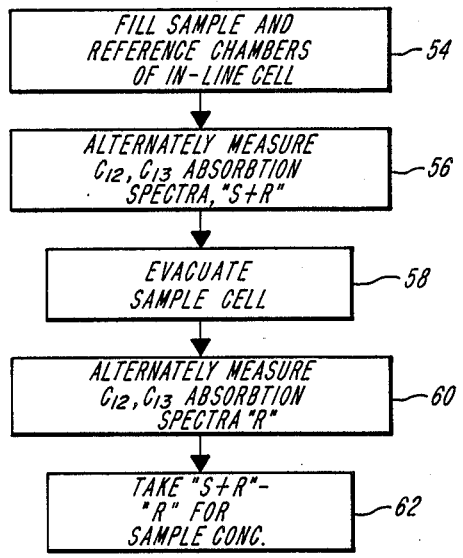
FIG. 4 is a process flow diagram illustrating the steps in obtaining isotopic concentration ratios in accordance with the present invention.

In operation, and referring now to FIG. 4, isotopic measurements as Provided by the instant invention are simply and quickly performed. In the typical case, the measurements can be quickly made in a matter of minutes, unlike the time consumed by the prior art devices, which often required separate standard sample measurements and consumption of specially prepared and expensive standard samples for the same determinations.

As shown by a block 54, for the exemplary $C_{12}$ and $C_{13}$ isotope measurements, the in-line absorption cell is so filled that the reference chamber 28 contains a known concentration of $C_{12}/C_{13}$ gas and the sample chamber 30 contains a gas having a $C_{12}/C_{13}$ isotope ratio to be determined.

As shown by a block 56, the tunable laser is operative to first provide a laser emission which is frequency modulated about a center frequency of the $C_{12}$ absorption band a predetermined number of cycles, and then is operative to produce a laser emission which is frequency modulated about the center frequency of the absorption band of the $C_{13}$ absorption band another predetermined number of cycles. The several modulated laser emissions are thus provided alternatively for one or more repetitions, for the duration of data collection. As the laser emission corresponding to the exemplary $C_{12}/C_{13}$ absorption lines occupies different positions on the same spectral mode, the laser current is discretely changed between different current levels to cause the tunable laser to emit radiation at the center frequency of the $C_{12}$ species and at the center frequency of the $C_{13}$ species.

In the presently preferred embodiment, one thousand samples are taken of the absorption respectively at laser lines corresponding to the $C_{12}$ and $C_{13}$ absorption bands so that statistically significant concentrations are thereby calculated, each sample corresponding to a cycle of the laser modulation frequency. As the amplitude of the triangle wave cyclically sweeps through the center frequency of the corresponding absorption band, the detector produces cycle-to-cycle an electrical signal that has a minimum value. For each such sample point, the synchronous detectors 44, 46, and 48 provide the $I''$, $I'''$, and I signals. The processor 50 is operative to calculate an average value from the $I''$ and I signals representative of the concentration of the combined sample and reference cells $C_{12}/C_{13}$ absorption concentration in accordance with the equations described above.

As shown by a block 58, after the absorption data for the combined reference and sample cells are obtained, the sample cell is completely evacuated of the sample gas contained therein. Thereafter, the absorption data for the known concentration of the gas in the reference cell is obtained, by again computing the $I''$ and I signals ratio taking a statistically significant number of samples.

As shown by a block 62, the $C_{12}/C_{13}$ isotopic concentration of the sample gas is then determined by simply subtracting the concentration of the reference isotopic ratio from that of the reference and sample isotopic ratio.

Many modifications of the presently disclosed invention will become apparent to those skilled in the art without departing from the scope of the instant invention. For example, in a process of measuring a sample in a flowing gas system, periodic reference gas measurements would have to be done. In another approach, a beam splitter could be used to provide a beam on a reference cell, in a separate manner similar to that described in the U.S. Pat. No. 4,410,273.

What is claimed is:

1. A method for determining isotopic ratios by absorption spectrometry, comprising the steps of:
    aligning a sample gas having the isotopic ratio to be determined and a reference gas having a known isotopic ratio in thermodynamic equilibrium along an optical path;
    irradiating the sample and reference gases with a laser beam;
    measuring the absorption of the laser beam by the combined sample and reference gases;
    removing the sample gas from the optical path;
    irradiating the reference gas with the laser beam;
    measuring the absorption of the laser beam by the reference gas; and
    subtracting from the measurement of the combined sample and reference gases the measurement of the reference gas to provide the isotopic ratio of the sample gas.

2. The method for determining isotopic ratios by absorption spectrometry of claim 1, wherein said irradiating steps are accomplished by using a laser diode.

3. The method for determining isotopic ratios by absorption spectrometry of claim 1, wherein said measuring steps are accomplished by first detecting second derivative of laser beam absorption signal, then by detecting the intensity of the laser beam signal, and then by computing their ratio.

4. A single-beam self-normalizing laser spectrometer, comprising:
    temperature controlled means for providing tunable, frequency modulated laser lines along an optical path;
    temperature controlled in-line means positioned along the optical path for providing a reference gas receiving chamber in tandem with a sample gas receiving chamber along the optical path;
    temperature controlled means for providing an electrical signal representative of the absorbence of the frequency modulated laser emission by the in-line means;
    means responsive to the electrical signal for providing an absorption signal I representative of the minimum intensity of the electrical signal during absorption; and
    means responsive to the electrical signal for providing a signal $I''$ representative of the second derivative of the electrical signal;
    wherein said laser frequency is modulated by a triangle waveform.

* * * * *

UNITED STATES PATENT AND TRADEMARK OFFICE
CERTIFICATE OF CORRECTION

PATENT NO. : 4,937,448

DATED : June 26, 1990

INVENTOR(S) : Arlan W. Mantz, John C. O'Connell

It is certified that error appears in the above-identified patent and that said Letters Patent is hereby corrected as shown below:

Column 5, line 14
"tunable laser emission" should be --tunable laser lines--

Column 6, line 14
"I" and I"" should be --I' and I"--

Column 7, line 5
"I", and I" should be --I', and I--.

Signed and Sealed this

Tenth Day of December, 1991

Attest:

HARRY F. MANBECK, JR.

Attesting Officer

Commissioner of Patents and Trademarks